(12) United States Patent
Hiramatsu et al.

(10) Patent No.: US 9,219,827 B2
(45) Date of Patent: Dec. 22, 2015

(54) IMAGE INSPECTION SYSTEM AND IMAGE INSPECTION METHOD

(71) Applicant: FUJI XEROX CO., LTD., Tokyo (JP)

(72) Inventors: Takashi Hiramatsu, Ashigarakami-gun (JP); Kiyofumi Aikawa, Ashigarakami-gun (JP); Michio Kikuchi, Ashigarakami-gun (JP)

(73) Assignee: FUJI XEROX CO., LTD., Tokyo (JP)

( * ) Notice: Subject to any disclaimer, the term of this patent is extended or adjusted under 35 U.S.C. 154(b) by 2 days.

(21) Appl. No.: 14/031,987

(22) Filed: Sep. 19, 2013

(65) Prior Publication Data

US 2014/0293363 A1    Oct. 2, 2014

(30) Foreign Application Priority Data

Mar. 26, 2013  (JP) .................................. 2013-064995

(51) Int. Cl.
*H04N 1/00*       (2006.01)
*B41J 29/46*      (2006.01)
*G01N 21/88*      (2006.01)

(52) U.S. Cl.
CPC ............ *H04N 1/00005* (2013.01); *B41J 29/46* (2013.01); *H04N 1/0005* (2013.01); *H04N 1/00015* (2013.01); *H04N 1/00042* (2013.01); *H04N 1/00076* (2013.01); *H04N 1/00092* (2013.01); *G01N 2021/8864* (2013.01)

(58) Field of Classification Search
CPC .................. H04N 1/00092; G01N 2021/8864; G01N 21/8851; G06K 2209/01; G06K 9/00463; G06K 9/40; G06K 9/34; G06T 2207/20144; G06T 2207/30168; G06T 5/002

USPC .............. 358/3.26, 1.11, 1.18, 505, 531, 537, 358/538, 540, 463; 382/112, 176, 275
See application file for complete search history.

(56) References Cited

U.S. PATENT DOCUMENTS 6,035,072 A  *  3/2000  Read ............................ 382/275
6,233,364 B1 *  5/2001  Krainiouk et al. ............ 382/275
2003/0190169 A1  10/2003  Shibaki (Continued)

FOREIGN PATENT DOCUMENTS

JP      H06-210836 A       8/1994
JP      H10-232933 A       9/1998
JP      A-2002-36513       2/2002

(Continued)

OTHER PUBLICATIONS

Extended European Search Report issued in European Patent Application No. 13187834.0 dated Jul. 11, 2014.

(Continued)

*Primary Examiner* — Jamares Q Washington
(74) *Attorney, Agent, or Firm* — Oliff PLC (57) ABSTRACT

There is provided an image inspection system. An image reading unit reads a formed image which is formed on a recording medium based on original image data to generate read image data. A determination unit compares the read image data and the original image data to determine whether or not the formed image includes a defective region. An extraction unit extracts an image of characters present around the defective region from the read image data. An image display device displays the image of the characters and an image of the defective region such that both the images overlap with each other.

8 Claims, 8 Drawing Sheets

(56) References Cited

U.S. PATENT DOCUMENTS

2006/0110009 A1* 5/2006 Klassen .............. G06T 7/001 382/112
2012/0218587 A1   8/2012 Koike

FOREIGN PATENT DOCUMENTS

| JP | A-2005-205723 | 8/2005 |
|----|---------------|--------|
| JP | A-2005-271431 | 10/2005 |
| JP | 2007-033247 A | 2/2007 |
| JP | A-2009-202438 | 9/2009 |

OTHER PUBLICATIONS

Jul. 14, 2015 Office Action issued in Japanese Application No. 2013-064995.

* cited by examiner

IMAGE INSPECTION SYSTEM AND IMAGE INSPECTION METHOD

CROSS-REFERENCE TO RELATED APPLICATIONS

This application is based on and claims priority under 35 USC. §119 from Japanese Patent Application No. 2013-064995 filed on Mar. 26, 2013.

TECHNICAL FIELD

The present invention relates to an image inspection system and an image inspection method.

SUMMARY

According to an aspect of the exemplary embodiments of the present invention, there is provided an image inspection system comprising: an image reading unit that reads a formed image which is formed on a recording medium based on original image data to generate read image data an acquisition unit that acquires the original image data; a determination unit that compares the read image data generated by the image reading unit and the original image data acquired by the acquisition unit to determine whether or not the formed image includes a defective region; an extraction unit that extracts an image of characters which are present around the defective region from the read image data according to a predetermined rule when the determination unit determines that the formed image includes the defective region; and an image display device that displays the image of the characters, extracted by the extraction unit and an image of the defective region such that both the images overlap with each other.

BRIEF DESCRIPTION OF THE DRAWINGS

Exemplary embodiments of the present invention will be described in detailed based on the following figures, wherein.

DETAILED DESCRIPTION

Figure 1:
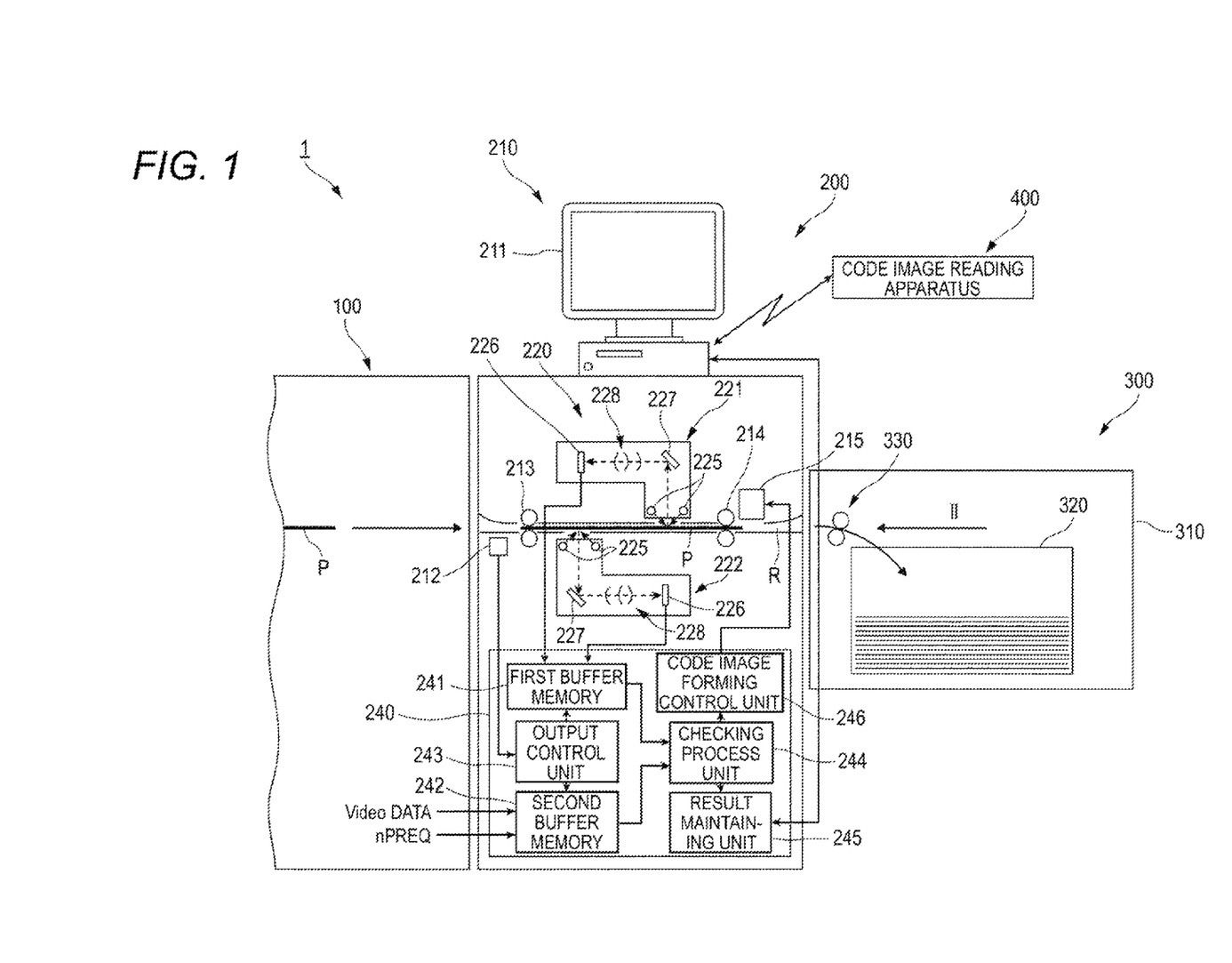
FIG. 1 is a view illustrating the overall configuration of an image forming system according to an exemplary embodiment.

Hereinafter, exemplary embodiments of the present invention will be described with reference to the accompanying drawings. FIG. 1 is a view illustrating the overall configuration of an image forming system according to the exemplary embodiment. The image forming system 1 of the present exemplary embodiment includes an image forming apparatus 100 that forms an image on a paper P which is an example of a recording medium, an inspection apparatus 200 which is an example of an image inspection system that inspects the image formed on the paper P by the image forming apparatus 100, and a paper receiving apparatus 300 that receives the paper P discharged from the inspection apparatus 200. In addition, the image forming system 1 is provided with a code image reading apparatus 400 that reads a code image (to described later in detail) formed on the paper P by the inspection apparatus 200.

The image forming apparatus 100 acquires image data (hereinafter, referred to as original image data), which serves as a basis for an image to be formed, from a Personal Computer (PC) (not illustrated) or the like, and forms the image on a paper P using an image forming material, such as toner, etc., based on the acquired original image data. In addition, in the present exemplary embodiment, for a mechanism of funning an image on a paper P, various other conventional methods, such as so-called an electrophotographic method, an inkjet method, etc., may be used without being particularly limited.

The inspection apparatus 200 is provided with a terminal device 210 that includes a touch panel type monitor 211 to receive an operation from a user (operator) and at the same time, to display information for the user. In addition, the inspection apparatus 200 is provided with a paper conveyance path R, along which a paper P discharged from the image forming apparatus 100 is conveyed. The inspection apparatus 200 is also provided with an edge detection sensor 212 placed beside the paper conveyance path R to detect an edge of a leading end portion of the paper P, and a first feeding roller 213 that feeds the paper P which has passed through the edge detection sensor 212 to a further downstream side.

In addition, the inspection apparatus 200 is provided with a second feeding roller 214 which is located at the downstream side of the first feeding roller 213 in the conveyance direction of the paper P and feeds the paper P to the further downstream side. An image reading device 220 that reads the image formed on the paper P is provided at the downstream site of the first feeding roller 213 and at the upstream side of the second feeding roller 214.

A code image forming head 215 that form a code image on a paper P present in the paper conveyance path R is provided at the downstream side of the second feeding roller 214. In addition, the inspection apparatus 200 is provided with a control unit 240 that controls a code image forming process by the code image forming head 215. The code image forming head 215 is configured by, for example, an inkjet head.

The image reading device 220 includes a front surface image reading device 221, which is located at one side of the paper conveyance path R (in the drawing, at the upper side of the paper conveyance path R) and reads an image formed on the front surface of a paper P, and a rear surface image reading device 222, which is located at the other side of the paper conveyance path R (in the drawing, at the lower side of the paper conveyance path R) and reads an image formed on the rear surface of the paper P.

Here, each of the front surface image reading device 221 and the rear surface image reading device 222 includes a light source 225 that emits light to the paper P, a line sensor 226 which receives light reflected from the paper P using a plurality of light receiving elements and generates image data (hereinafter referred to as "read image data"), and is reflective mirror 227 that guides the reflected light from the paper P to the line sensor 226. In addition, each image reading device includes an imaging optical system 228 that concentrates the reflected light from the paper P, which is guided by the reflective mirror 227, on the line sensor 226. In the present exemplary embodiment, the front surface image reading device 221 and the rear surface image reading device 222 function as an image reading unit that reads a formed image which is formed on the paper P based on the original image data to generate read image data.

Next, a control unit 240 will be described. The control unit 240 is provided with a first buffer memory 241 that accumulates read image data output from the front surface image reading device 221 and the rear surface image reading device 222. In addition, the control unit 240 is provided with a second buffer memory 242 that accumulates the original image data transmitted from the image forming apparatus 100, the PC (not shown), or the like. In the present exemplary embodiment, the second buffer memory 242 functions as an acquisition unit that acquires the original image data.

In addition, the control unit 240 includes an output control unit 243 that controls the output of image data (original image data and read image data from the first buffer memory 241 and the second buffer memory 242 to a checking process unit 244. In the present exemplary embodiment, the checking process unit 244 conducts checking of the read image data and the original image data. In order to conduct the checking more easily, it is desirable to conduct a processing, e.g., a grayscale conversion or a resolution conversion, on the original image data, for example, when the original image data is stored in the second buffer memory 242.

Here, the output control unit 243 controls the output of image data from the first buffer memory 241 and the second buffer memory 242 in such a manner that the output timing of read image data stored in the first buffer memory 242 from the first buffer memory 241 and the output timing of original image data stored in the second buffer memory 242 from the second buffer memory become equal to each other.

More specifically, the output control unit 243 allows the original image data and read image data to be sequentially output from the first buffer memory 241 and the second buffer memory 242 by one page (one paper), in which case (when the output of image data of each page begins), for example, the output is initiated from the image data corresponding to an image to be formed at the leading end of each page, and the image data corresponding to the image to be formed at the trailing end of each page is finally output.

In addition, in the present exemplary embodiment, the output start timing of the read image data from the first buffer memory 241 and the output start timing of the original image data from the second buffer memory 242 are made to coincide with each other and at the same time, when the image data corresponding to the image to be formed at the trailing end of each page is output, the output timing of the road image data and the output timing of the original image data are made to coincide with each other. Thus, in the present exemplary embodiment, when the original image data and the read image data are compared by the checking process unit 244, a position of an image on the paper P specified by the original image data and a position of an image on the paper P specified by read image data are made to coincide with each other.

In addition, in the present exemplary embodiment, the output of the edge detection sensor 212 is output to the output control unit 243, and the output control unit 243 checks whether or not the leading end of the paper P reaches the edge detection sensor 212. A dock signal synchronized with image reading is transmitted from the line sensor 226 to the first buffer memory 241 together with the read image data. Further, a page synchronized signal (a signal used to specify which part in information transmitted from as PC, etc. corresponds to the original image data) is transmitted to the second buffer memory 242 together with the original image data. The output control unit 243 determines the output timing of the original image data and the read image data based on the output of the edge detection sensor 212, the clock signal, and the page synchronized signal.

Further referring to the control unit 240, the control unit 240 is provided with a checking process unit 244 which checks the read image data output from the first buffet memory 241 and the original image data output from the second buffer memory 242. In addition, a result maintaining unit 245 is provided to maintain the checking result of the checking process unit 244. In addition, a code image forming control unit 246 is provided to control the code image forming head 215 based on the checking result of the checking process unit 244.

The checking process unit 244 divides each of the read image data transmitted from the first buffer memory 241 and the original image data transmitted from the second buffer memory into predetermined regions, and at the same time, performs pattern matching for each region, thereby determining whether or not a defect occurring place (a defective region) is present in the formed image. In a typical pattern matching method, for example, two regions selected as comparison objects are compared with each other in terms of a predetermined parameter such as density, on a pixel basis, for a plurality of pixels included in each of the two regions, and a difference in parameter between the two regions is calculated. Then, the sum of absolute values of a plurality of differences obtained by comparing the respective pixels is calculated, and it is determined whether or not the sum of absolute values exceeds a predetermined threshold. Then, when the sum of absolute values exceeds the predetermined threshold, it is determined that a defect occurs in the image (at a portion of the image). In the present exemplary embodiment, the checking process unit 244 functions as a determination unit that compares the read image data generated by the front surface image reading device 221 and the rear surface image reading device 222 and the original image data acquired by the second buffer memory 242 to determine whether or not a defective region is included in a formed image.

Next, the paper receiving apparatus 300 will be described. The paper receiving apparatus 300 of the present exemplary embodiment is provided with a case 310. In addition, a paper stacking unit 320 is accommodated in the case 310 such that the papers P sequentially discharged and sent from the inspection device 200 are stacked in the paper stacking unit 320. In addition, a feeding roller 310 is installed to feed the papers P discharged from the inspection apparatus 200 to the paper stacking unit 320.

Figure 2:
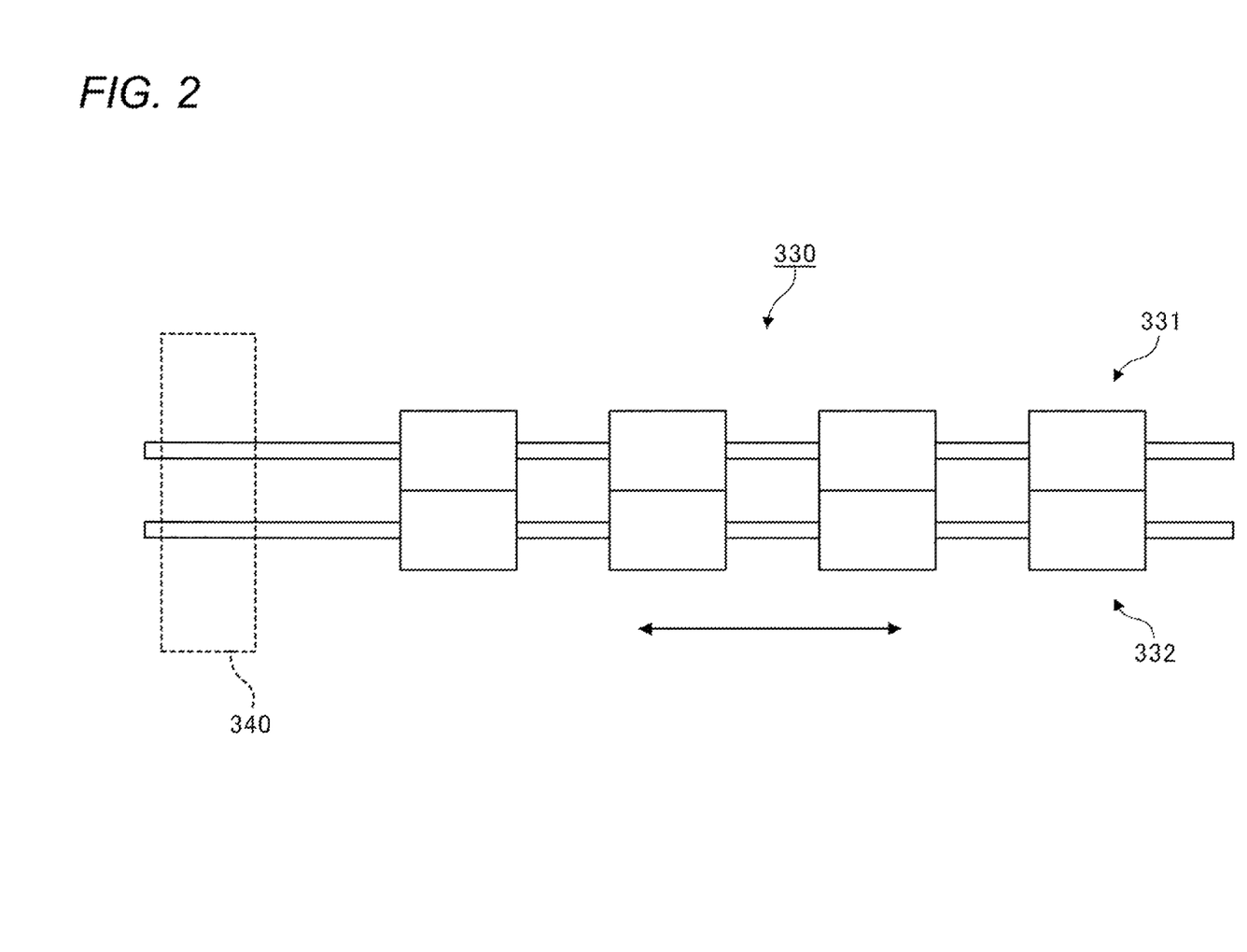
FIG. 2 is a view illustrating a feeding roller viewed in a direction designated by arrow II of FIG. 1.

In the present exemplary embodiment, as illustrated in FIG. 2 (illustrating the feeding roller 330 viewed in the direction of arrow II of FIG. 1), the feeding roller 330 includes a driving roller 331 that is rotated by a motor (not illustrated), and a driven roller 332 that is pressed by the driving roller 331 to be rotated following the driving roller 331. In the present exemplary embodiment, the feeding roller 330 is installed to be movable in the axial direction thereof.

In addition, the present exemplary embodiment is provided with a movement device 340 which includes, e.g., as motor or a cam (neither of which is illustrated) and moves the feeding roller 330 in the axial direction of the feeding roller 330. In the present exemplary embodiment, since the feeding roller 330 is moved in the axial direction thereof by the movement device 340, the stacking positions of papers P may be varied. In other words, the stacking positions of the papers P may be offset.

Figure 3:
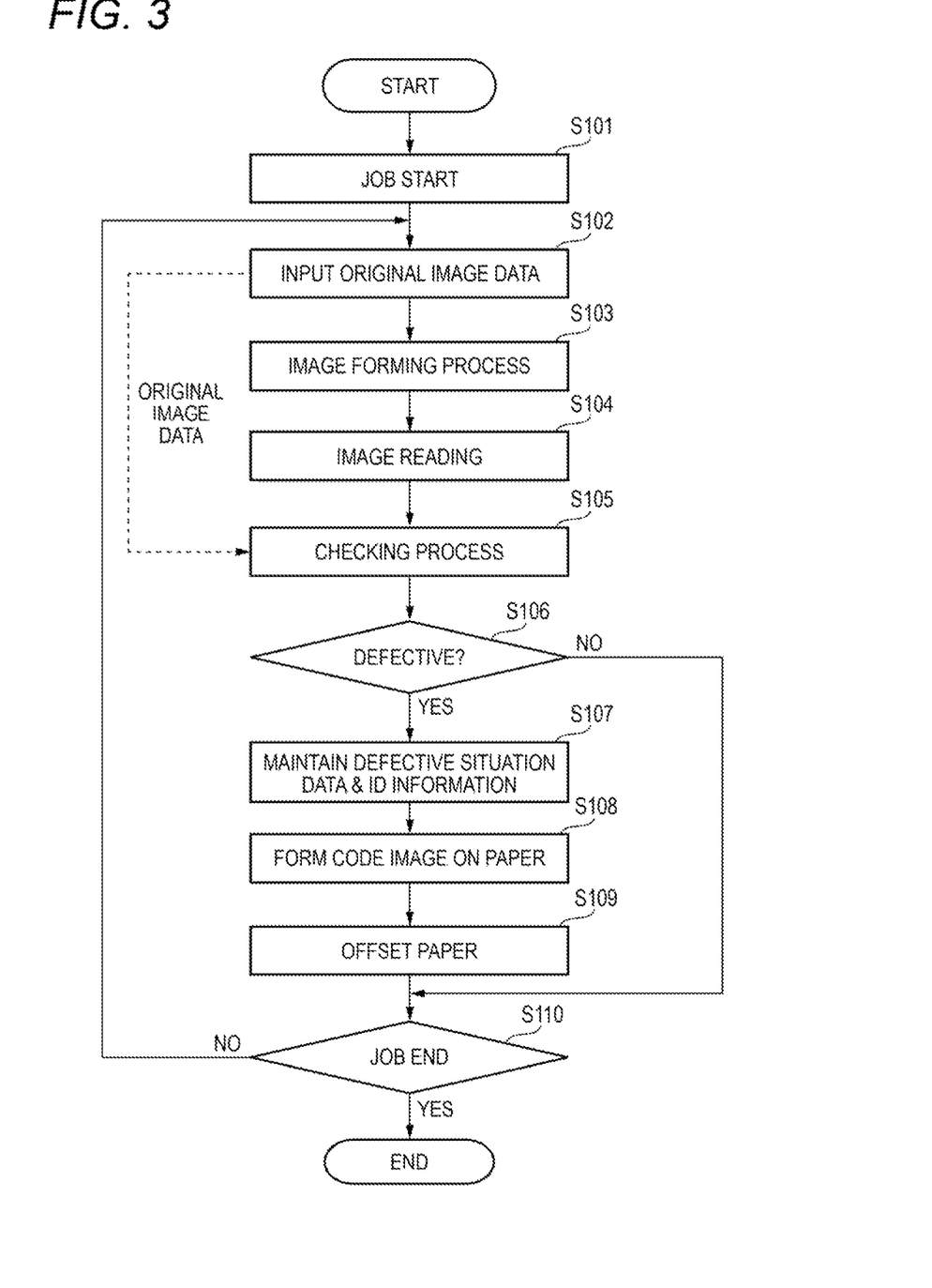
FIG. 3 is a flowchart illustrating the flow of a process executed by the image forming system of the exemplary embodiment.

FIG. 3 is a flowchart illustrating the flow of a process executed by the image forming system 1 according to an exemplary embodiment. In the present exemplary embodiment, an image forming process based on a printing job begins when a start button (not illustrated) is pressed by a user (step 101). More specifically, first, original image data provided by the user is input to the image forming apparatus 100 (step 102). As a result, the image forming process is executed in the image forming apparatus 100 (step 103). The original image data provided by the user is also stored in the second buffer memory 242 of the inspection apparatus 200 (see FIG. 1) so that the original image data may be used in a checking process to be described below.

Thereafter, the papers P, which are sequentially discharged from the image forming apparatus 100 according to the image forming process, are fed to the inspection apparatus 200, and the inspection device 200 reads the images on the papers P (step 104). Read image data acquired by the reading process are stored in the first buffer memory 241 illustrated in FIG. 1. Thereafter, in the present exemplary embodiment, the checking process unit 244 of the inspection apparatus 200 executes the checking process (step 105). More specifically, pattern matching is conducted using the read image data stored in the first buffer memory 241 and the original image data stored in the second buffer memory 242.

Subsequently, the checking process unit 244 determines, based on the pattern matching, whether or not a defect occurs on the images formed on the papers P (step 106). Then, when the checking processing unit 244 determines that no defect occurs, a main control unit (not illustrated) determines whether or not priming is entirely ended (step 110). When it is determined that the printing is entirely ended, the entire process is ended. On the other hand, if it is determined that the printing is not ended, the processings after step 102 are repeatedly executed.

Meanwhile, in step 106, when it is determined that a defect occurs, the checking process unit 244 matches defect situation data including, e.g., page information regarding a defect occurring page (page number), a defect occurring position (a position in a page), a defective level, the number of defects, original image data, and read image data, to identification information (ID) for identifying the defect situation data from other defect situation data, and then, outputs the defect situation data and identification information to the result maintaining unit 245.

As a result, the related defect situation data and identification information are maintained by the result maintaining unit 245 (step 107). At this time, as will be described in detail below, the result maintaining unit 245 extracts and maintains some of the original image data and the read image data. Thereafter, the code image forming control unit 246 (see FIG. 1) generates a code image based on the identification information, and forms the generated code image on a paper P that is determined as a defect occurring page using the code image forming head 215 (step 108).

Further, the papers P formed with the code images are stacked in the paper stacking unit 320 (see FIG. 1). However, in this case, the feeding roller 330 is moved by the movement device 340 (see FIG. 2) such that the papers P formed with the code images are stacked in the paper stacking unit 320 in an offset state (step 109). Thereafter, it is determined whether or not the printing job is ended in step 110, and when it is determined that the printing job is entirely ended, the entire processing is ended. On the other hand, when it is determined than the printing job is not ended, the processes after step 102 are repeatedly executed.

Figure 4:
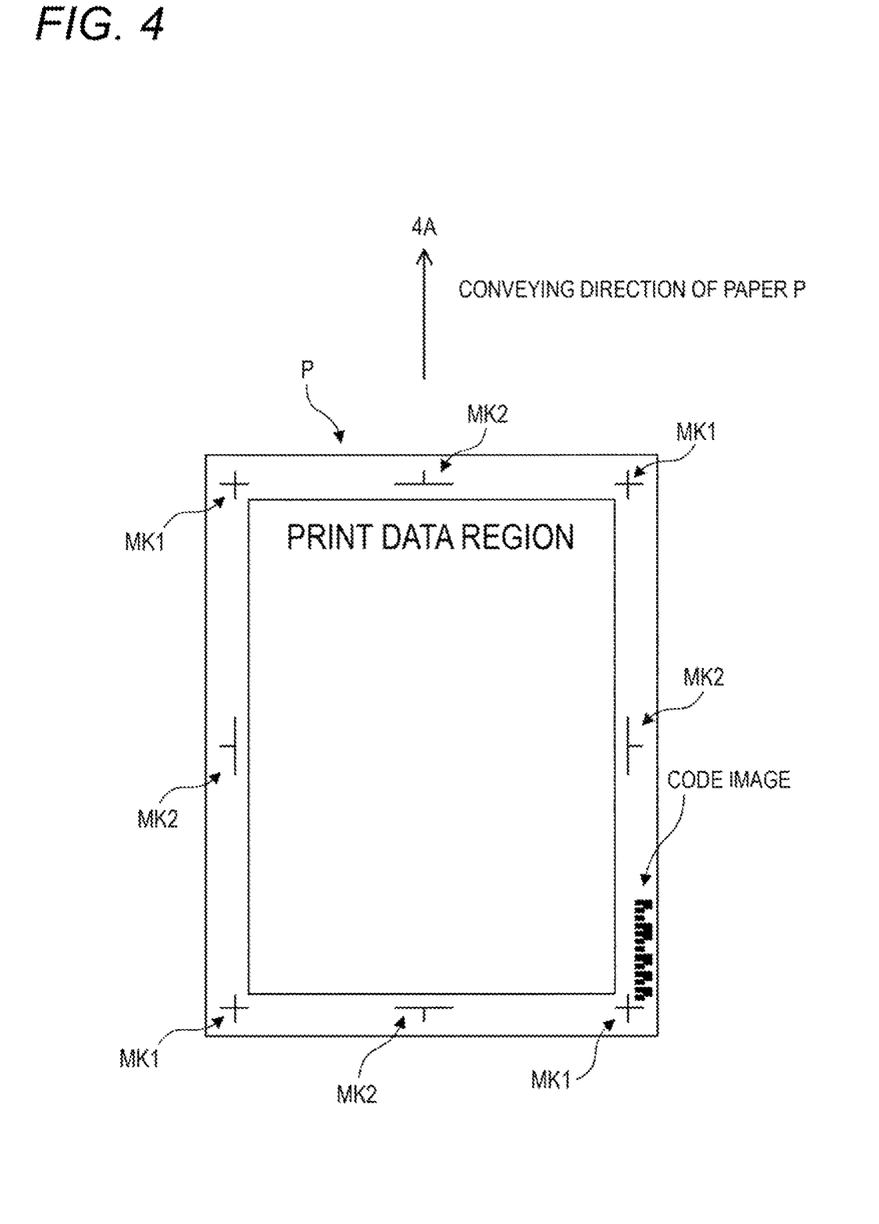
FIG. 4 is a view illustrating a code image formed on a paper.

FIG. 4 is a view illustrating a code image formed on a paper P. In the present exemplary embodiment, the image forming apparatus 100 forms an image in a rectangular region illustrated as "PRINT DATA REGION" in the drawing. In addition, as illustrated in the same drawing, the image forming apparatus 100 forms (prima) cross-shaped marks MK1 at the four corners of the rectangular paper at the places positioned outside the "PRINT DATA REGION".

In the present exemplary embodiment, a T-shaped mark MK2 is thrilled between neighboring cross-shaped marks MK1. Here, in the present exemplary embodiment, the regions outside the marks MK1 and MK2 are cut away when bookbinding, for example. In addition, in the present exemplary embodiment the code image is formed on a cut-away portion. Thus, in the present exemplary embodiment, it is possible to prevent the paper P front being bound in a state in which the code image remains on the paper P. As for the code image, for example, a one-dimensional barcode or a two-dimensional barcode such as a QR code (registered trademark) may be used although not particularly limited thereto.

Here, in the present exemplary embodiment, the code image is formed at the trailing end side of the paper P in a conveying direction along which the paper P is conveyed (a paper conveying direction of the inspection apparatus 200, i.e., in the conveying direction as illustrated by arrow 4A in FIG. 4). Here, in order to miniaturize the inspection apparatus 200 (see FIG. 1), it is desirable to dispose, the code image forming head 215 at a further upstream side in the conveying direction of the paper P so that the code image forming head may be located close to the image reading device 220. On the other hand, if the code image forming head 215 is excessively close to the image reading device 220, a problem may occur in that, when the code image is formed by the code image forming head 215, the paper P may be located downstream of the code image forming head 215 and thus, the code image may not be formed.

For this reason, the present exemplary embodiment seeks miniaturization of the inspection apparatus 200 while suppressing the occurrence of the above-described problem by locating the code image forming head 215 at the most upstream side among places where the formation of the code image on the paper P by the code image forming head 215 becomes enabled. Moreover, in this case, the code image is formed at the trailing end of the paper P in the conveying direction of the paper P.

After the formation of the image on the paper P is ended, in the present exemplary embodiment, the quality of an image that has been determined as a defect occurring image may be confirmed by the tree in some cases. In such a case, in the present exemplary embodiment, first, the paper P formed with an image which has been determined, as a detect occurring image (the paper formed with the image that has been determined as a defect occurring image by the to inspection apparatus 200) (hereinafter, referred to as a "defective paper P" in some cases) among the papers P stacked in the paper stacking unit 320 (see FIG. 1) is found by the user. Here, in the present exemplary embodiment, the code image is formed at a side portion of the defective paper P, and the user will find the defective paper P based on the presence/absence of the code image.

Thereafter, in the present exemplary embodiment, as the code image reading apparatus 400 illustrated in FIG. 1 is operated by the user, the code image on the defective paper P is read. In addition, the code image reading apparatus 400 is configured as a movable apparatus, and the code image reading is conducted in a state in which the defective paper P is stacked in the paper stacking unit 320. In addition, since the defective paper P may remain in the paper stacking unit 320 as it is without being removed according to the defective level, in the present exemplary embodiment, the user reads the code image from the defective paper P in a state in which the defective paper P is still stacked in the paper stacking unit 320. A barcode reader is an example of the code image reading apparatus 400. In addition, the present exemplary embodiment may be configured to use, for example, a camera equipped portable phone or a smart phone as the code image recording apparatus 400 without being limited to a dedicated device such as the bar code reader.

Then, when the code image reading on the defective paper P is carried out, information regarding defects is displayed on the monitor 211 (see FIG. 1). That is, it is difficult for the inspection apparatus 200 to conduct a subjective inspection as if the inspection is performed by a person. Therefore, even if an image is determined as a defect occurring image by the inspection apparatus 200, in some cases, it may be determined that no defect occurs when the image is determined by a person. In such a situation, it is not reasonable that an image determined as being defective by the inspection apparatus 200 is discarded in all the cases. For example, when a defective region is in a shape of a small dot, the inspection apparatus 200 determines that a defect occurs in the formed image for the defective region. However, in general, such a defective region may not be problematic in many cases. However, when such a dot-shaped defective region has occurred at a place where a numerical value is printed as a formed image, it is feared that a person who sees the defective region may erroneously recognize the defective region as a decimal point. Accordingly, in this case, it is good to determine the flamed image as being defective. Thus, even in the case in which the formed image is determined as being defective by the inspection apparatus 200, confirmation by the user becomes desired. To this end, in the present exemplary embodiment, information regarding a defect is displayed on the monitor 211 so that the user may conduct inspection again with the eyes.

However, when all the images based on the original image data as well as the images based on the read image data are displayed, even the information needed to be kept secret such as personal information will be displayed on the monitor 211. Thus, there is possibility that the information needed to be kept secret may be known to the user who operates the inspection apparatus 200. Accordingly, the prose exemplary embodiment seeks to suppress such a problem by extracting a part of an image based on the original image data or an image based on the read image data and displaying the part on the monitor 211 in the following manner.

Figure 5:
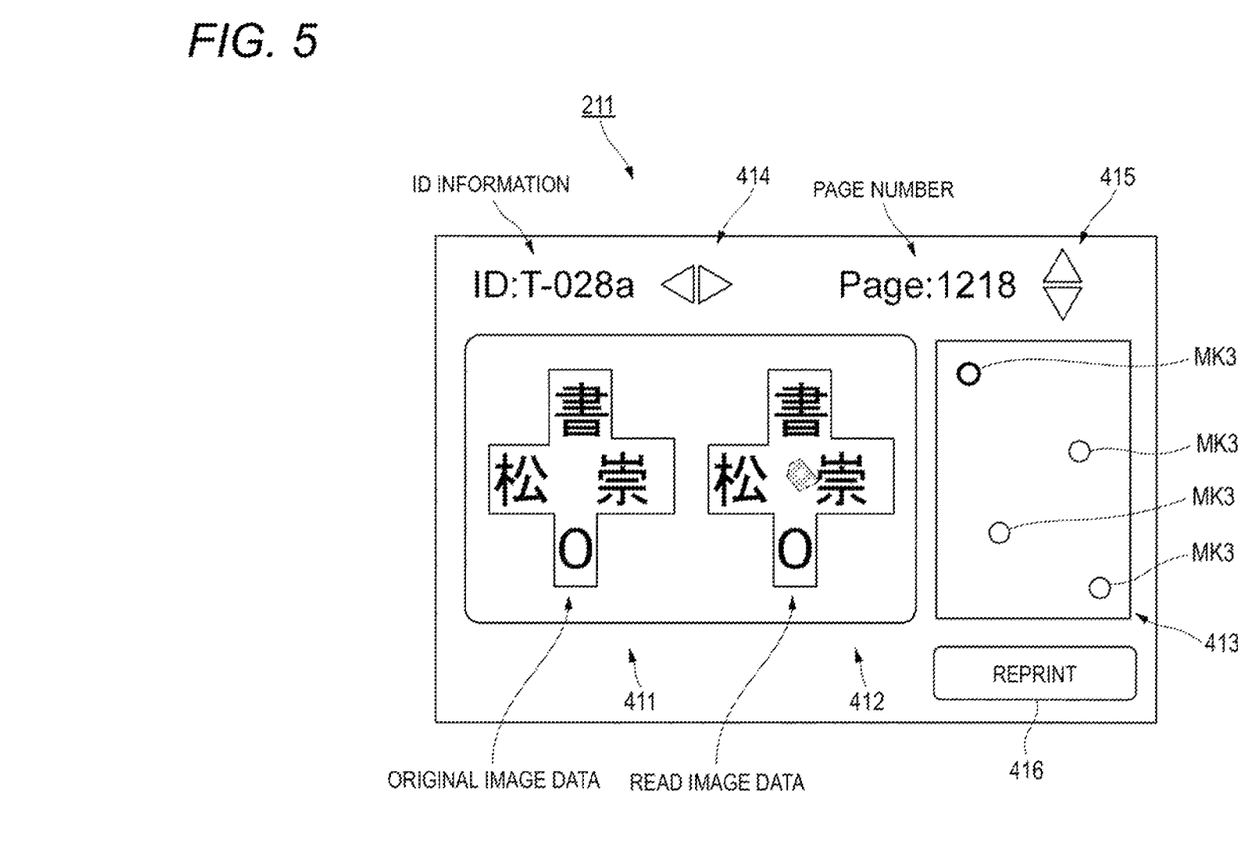
FIG. 5 is a view illustrating one example of a display screen of a monitor.

FIG. 5 is a view illustrating an example of a display screen of the monitor 211. In the present exemplary embodiment, the above-described identification information (ID) acquired by reading a code image is displayed on the top left of the drawing of the display screen in the monitor 211. In addition, the page number of a page currently displayed on the display screen is displayed on the top right of the display screen.

In addition, in the present exemplary embodiment, a magnification display unit 412 which magnifies and displays a defect occurring place is provided at the center of a middle portion of the display screen. In more detail, the magnification display unit 412 which magnifies and displays an image based on the read image data of a defect occurring place is provided at the center of the middle portion of the display screen.

Further, in the present exemplary embodiment, an original image display unit 411 which displays an image based on the original image data is provided at the left side of the middle section of the display screen (on the left of the magnification display unit 412). In more detail, the original image display unit 411 which magnifies and displays an image based on the original image data corresponding to a defect occurring place among the original image data is provided at the left side of the middle section of the display screen. In the present exemplary embodiment, the magnification display unit 412 and the original image display unit 411 are displayed adjacent to each other as described above, so that an image displayed on the magnification display unit 412 and an image displayed on the original image display unit 411 may be easily compared.

In addition, in the present exemplary embodiment, a full image 413 of the currently displayed page is displayed at the right side of the middle portion of the display screen. However, the contents of the currently displayed page are not displayed here and only a defect occurring place in the page is displayed. In FIG. 5, four circular marks MK3 are indicated in the full image, representing that defects occur at the places where the marks MK3 are indicated. That is, the page is displayed as a blank paper except the four marks MK3. Among the four marks MK3, the mark MK3 surrounding a defect (defective image) displayed on the magnification display unit 412 (the uppermost mark MK3 in the drawing) is indicated by a bold line to highlight. As such, it becomes easy for the user to recognize which defect is magnified and displayed in the magnification display unit 412 among a plurality of displayed defects.

The full image 413 of the page may be displayed in a resolution roughened to a level where a character cannot be recognized. In addition, a high security region such as personal information may be acquired from the original image data and the characters of the region may be masked and displayed. In this case, the region may be wholly painted with a predetermined color, or instead, a character string such as "PERSONAL INFORMATION" may be displayed in the region. Alternatively, there will be no problems even if full image 413 of the page itself is not displayed.

In a case in which two or more defect occurring places are present in the same page and are close to each other, personal information such as a name may be recognized by the user when all the defect occurring places are displayed. For this reason in such a case, it is desirable to display only one of the defect occurring places on the original image display unit 411 and the magnification display unit 412. That is, assuming that in information regarding as name called, for example, "平松 崇" (Japanese characters indicating "HIRA-MATSU-TAKASHI"), one defect occurring place is present between "平" (Japanese character indicating "HIRA") and "松" (Japanese character indicating "MATSU") and another defect occurring place is present between "松" ("MATSU") and "崇" (Japanese character indicating "TAKASHI"), the user may recognize the entire information of the name called "平松崇" ("HIRA-MATSU-TAKASHI") when the regions are successively read. Accordingly, in this case, it is desirable to display the more defective one without displaying the other place, for example. Likewise, even in the case in which one defect is present across two or more character strings, it is desirable to display only one region around any one character in the original image display unit 411 and the magnification display unit 412.

On the right of the identification information displayed place, there is provided a switching operation unit 414 indicated by two triangles and operated by the user when switching from one defective place displayed on the magnification display unit 412 to another defective place. Similarly, on the right of the page number displayed place, there is provided a page-switching operation unit 415 indicated by two triangles and operated (pressed) by the user when switching from one page to another page.

In the present exemplary embodiment, a reprint button 416 operated (pressed) by the user when the user wishes to reprint the same page is displayed on the bottom right of the display screen as illustrated in the drawing. Here, when the user determines that a defect exceeding a limitation occurs as a result of confirming the display screen, the user presses the reprint button 416. In addition, when the reprint button 416 is pressed, image forming is performed with the image thrilling apparatus 100 (FIG. 1), and a new paper P formed with an image is stacked in the paper stacking unit 320.

Hereinafter, an image displayed in the magnification display unit 412 will be described in more detail. In the example illustrated in FIG. 5, an image of characters present around a defective region is extracted from read image data, and the extracted character image is displayed together with an image of a defective region such that the images of the characters and the defective region overlap each other. The extraction of the character image is carried out according to a predetermined rule.

Figure 6A:
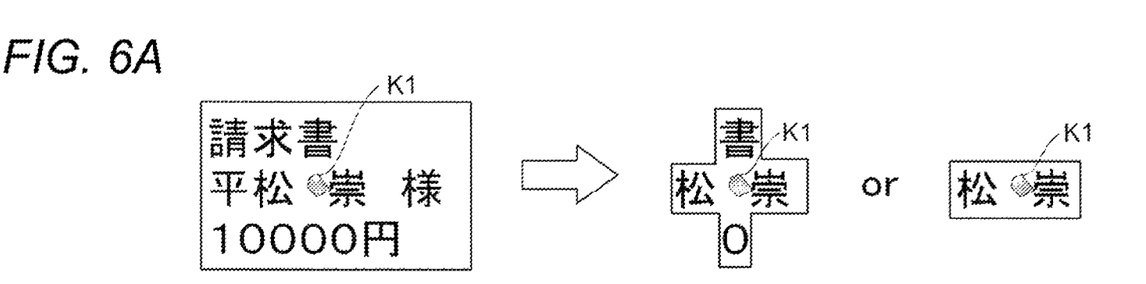
FIGS. 6A to 6C are explanatory views illustrating a first example of a method of extracting a character image.
Figure 6B:
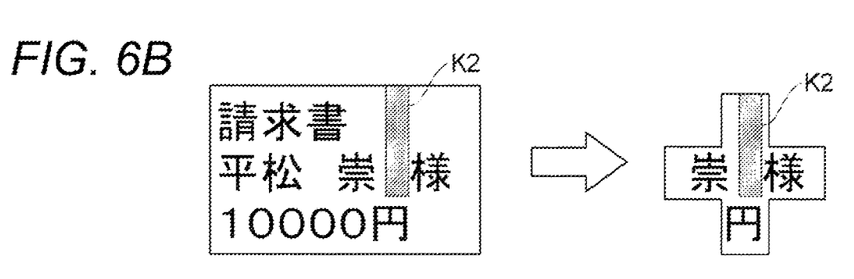
Figure 6C:
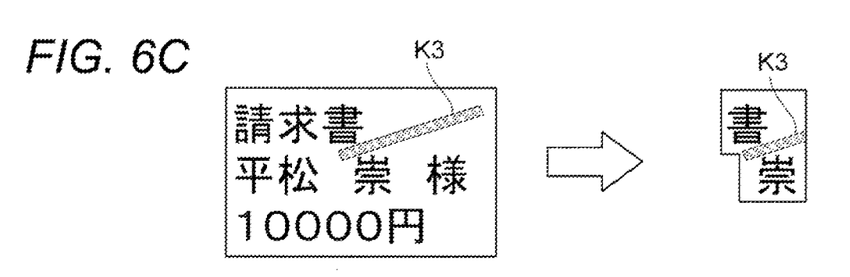

FIGS. 6A to 6C illustrate a first example explaining a method of extracting a character image. The first example illustrates diameter image extracted when a defective region does not overlap with a character. More specifically, in the present exemplary embodiment, when a defective region does not overlap with a character, a character image of at least two characters among the characters closely present at upper and lower sides and left and right sides of the detective region is extracted.

FIG. 6A illustrates an image around a defective region K1 at the left side. In addition, at the right side of the drawing, the character images extracted from the image of the left side are illustrated. In this case, for example, four characters present at upper and lower sides and left and right sides of the defective region K1 are extracted. More specifically, four characters, "徵" (Japanese character indicating "SYO"). "0" (zero), "松" (Japanese character indicating "MATSU") and "隆" (Japanese character indicating "TAKASHI"), are extracted. In other words, it may be described that a character image is extracted from a cross-shaped region around the defective region K1. Here, for example, two characters present on the left and right of the defective region K1 may be extracted. More specifically, two characters, "松" ("MASTU") and "隆" ("TAKASHI"), may be extracted. That is, two characters close to each other around the defective region K1 in the row direction may be extracted. In addition, although not illustrated, two characters present at upper and lower sides of the defective region K1. In this case, more specifically, two characters, "徵" and "0" (zero) may be extracted. That is, two characters close to each other around the defective region K1 in the column direction may be extracted.

Similar to FIG. 6A, FIG. 6B illustrates an image of a region around a defective region K2 at the left side. In addition, at the right side of the drawing, a character image extracted from the image of the left side is extracted. In this case, three characters present at lower, left and right sides of the defective region K2 are extracted. More specifically, three characters, "円" (Japanese character indicating "YEN"), "隆" ("TAKASHI") and "様" (Japanese character indicating "SAMA"), are extracted. In this example, although no character is present at the upper side and thus, character extraction is not performed, an image of a defective region K2 is displayed at the corresponding portion. Also in this case, it may be described that a character image is extracted from a cross-shaped region around the defective region K2.

FIG. 6C illustrates an example of extracting an image of characters which are located within a distance of a predetermined value from a defective region K3 on the recording material. At the left side of FIG. 6C, an image of a region around the defective region K3 is illustrated. In addition, at the right side of FIG. 6C, a character image extracted from the image of the left side is illustrated. This is an example in which extraction of one character, "様" ("SAMA") is not performed since the two characters, "徵" ("SYO") and "隆" ("TAKASHI"), are near to the defective region K3 but the character, "様" ("SAMA"), is distant from the defective region K3.

When the images of the left site of FIGS. 6A to 6C are displayed on the monitor 211, the user who sees the image may grasp that the page means a "請求書" (Japanese characters indicating "SEI-KYU-SYO" which means a bill), the billing destination is "平松 隆様" (Japanese characters indicating "HIRA-MATSU-TAKASHI-SAMA" which means Mr. Takashi Hiramatsu), and the billing amount is "1 0 0 0 0 円" (Japanese characters indicating "10000 YEN" which means 10,000 Japanese Yen). Meanwhile, when the character images as illustrated at the right side of FIGS. 6A to 6C are extracted, it is difficult for the user to grasp the contents even if the images are displayed on the monitor 211. In this case, the images of the defective regions and the regions around the detective regions are also displayed. In the present exemplary embodiment, by seeing the relationship between the defective region and at least two characters close to the defective region, it is determined whether or not the defective region prevents transmission or information to a person seeing the page. Displaying the extracted regions may be sufficient for determining whether or not transmission of information is prevented, and trouble is hardly caused with respect to the user's job of determining whether or not a defective region has a defect exceeding a limitation.

Figure 7A:
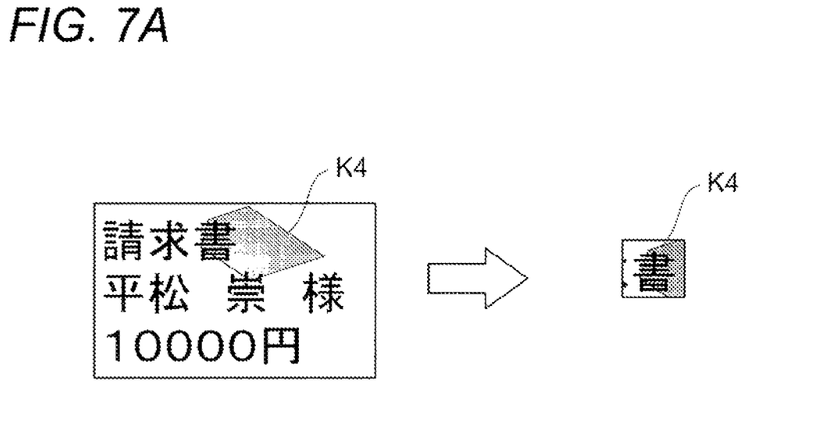
FIGS. 7A and 7B are explanatory views illustrating a second example of a method of extracting a character image.
Figure 7B:
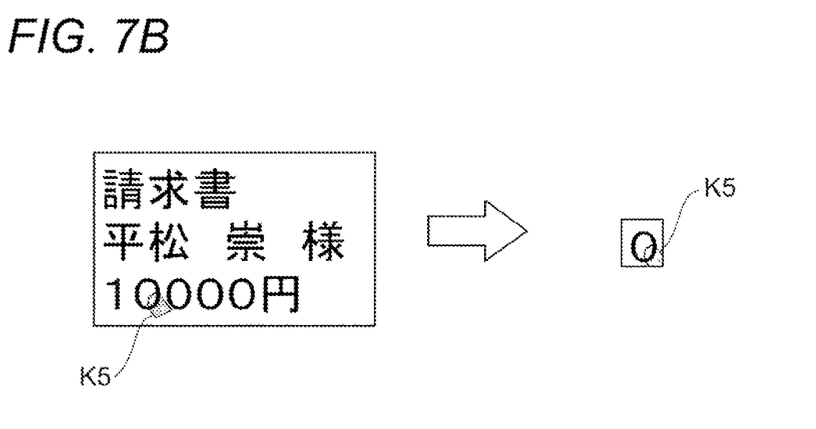

FIGS. 7A and 7B illustrate a second example of a method of extracting a character image. The second example illustrates character images extracted when a defective region and a character overlap each other. More specifically, in the present exemplary embodiment, when a defective, region and characters overlap each other, one character which has the greatest overlap with the defective region is extracted.

FIG. 7A illustrates an image of a region around a defective region K4 at the left side. In addition, at the right side of the drawing, a character image extracted from the image of the left side is illustrated. In this case, the detective region K4 overlaps with two characters, "徵" ("SYO") and "隆" ("TAKASHI"). However, the character, "徵" ("SYO"), has a greater overlap with the defective region K4 than "隆" ("TAKASHI"). Therefore, the one character, "徵" ("SYO"), is extracted.

Similarly, FIG. 7B illustrates an image of a region around a defective region K5 at the left side. In addition, at the right side of the drawing, a character image extracted from the image of the left side is illustrated. In this case, since the defective region K5 overlaps with only one character, "0" (zero), the one character, "0" (zero) is extracted.

When the character images as illustrated at the right side of FIGS. 7A and 7B are extracted, it is difficult for the user to grasp the contents the pages even if the images are displayed on the monitor 211. In addition, in the present exemplary embodiment, an image of one character which has the greatest overlap with the defective region is extracted. As a result, a region which is prone to be determined as the most defective one may be selectively extracted. In addition, since the extracted image has one character, it becomes more difficult for the user to grasp the contents of the page.

The extraction of a character image as described above is carried out by the result maintaining unit 245. Accordingly, in the present exemplary embodiment, when the checking, process unit 244 determines that a formed image has a defective region, the result maintaining unit 245 functions as an extraction unit that extracts a character image present around the defective region from the read image data according to a predetermined rule.

Figure 8:
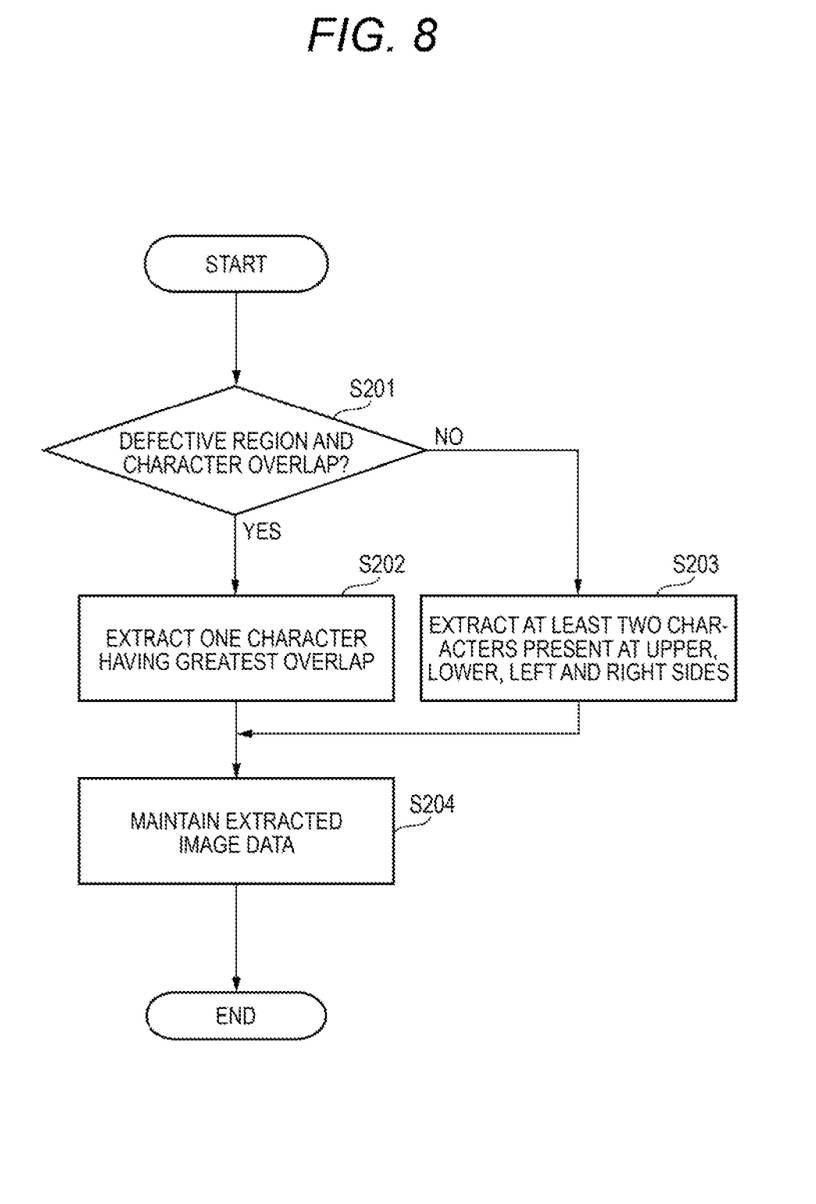
FIG. 8 is a flowchart illustrating as sequence of extracting a character image by a result maintaining unit.

FIG. 8 is a flowchart illustrating the sequence of extracting a character image by the result maintaining unit 245. Specifically, the flowchart of FIG. 8 corresponds to a part of a processing carried out in step 107.

First, when it is determined that a defect occurs in a formed image, the result maintaining unit 245 determines whether or not an overlap between the defective region and characters has occurred (step 201).

Then, when the overlap between the defective region and characters has occurred ("Yes" in step 201), the result maintaining unit 245 extracts an image of one character which has the greatest overlap with the defective region among the overlapped characters as illustrated in FIGS. 7A and 7B (step 202).

Meanwhile, when the defective region does not overlap with characters ("No" in step 201), the result maintaining unit 245, as illustrated in FIGS. 6A to 6C, extracts at least two characters among the characters closely present at upper and lower sides and left and right sides of the defective region (step 203). In this case, as illustrated in FIG. 6A, the four characters present at upper and lower sides and left and right sides may be extracted, or two characters present in the row direction or in the column direction may be extracted. In addition, when no character is present in any direction, as illustrated in FIG. 6B, extraction of the defective region instead of characters may be carried out. Further, as illustrated in FIG. 6C, it may be set such that an image of two characters which are located within a distance of a predetermined value from the defective region on the paper P is extracted and an image of a character which is located at a distance exceeding the predetermined value from the defective region on the paper P is not extracted.

Then, the result maintaining unit 245 performs a processing for maintaining the original image data and read image data related to the extracted character images (step 204).

The processings conducted by the control unit 240 in the present exemplary embodiment may be implemented when software and hardware resources cooperate with each other. That is, an internal CPU (not illustrated) within a computer for control use provided in the control unit 240 may execute a program, which implements respective functions of the control unit 240, so as to implement the respective functions.

Accordingly, the processings conducted by the control unit 240 may be grasped as a computer program that implements, in a computer, a function of reading an image formed on a paper P based on original image data to generate read image data, a function of acquiring original image data, a function of determining whether or not the formed image has a defective region by comparing the generated read image data and the acquired original image data, and a function of extracting an image of characters present around the defective region according to a predetermined rule when it is determined that the image has the defective region.

In the above-described examples, a paper P determined as being defective and formed with a code image is stacked in the paper stacking unit 320 in an offset state but not limited thereto. For example, two paper stacking units 320 may be provided so that papers P determined as defect occurring ones and papers P determined as non-defect occurring ones may be sorted. In addition, an interleaving paper may be interposed between the papers without offsetting.

The foregoing description of the exemplary embodiments of the present invention has been provided for the purposes of illustration and description. It is not intended to be exhaustive or to limit the invention to the precise forms disclosed. Obviously, many modifications and variations will be apparent to practitioners skilled in the art. The embodiments were chosen and described in order to best explain the principles of the invention and its practical applications, thereby enabling others skilled in the art to understand the invention for various embodiments and with the various modifications as are suited to the particular use contemplated. It is intended that the scope of the invention be defined by the following claims and their equivalents.

What is claimed is:

1. An image inspection system comprising:
   an image reading unit that reads a formed image which is formed on a recording medium based on original image data to generate read image data;
   an acquisition unit that acquires the original image data;
   a determination unit that compares the read image data generated by the image reading unit and the original image data acquired by the acquisition unit to determine whether or not the formed image includes a defective region;
   an extraction unit that extracts an image of characters which are present around the defective region from the read image data according to a predetermined rule when the determination unit determines that the formed image includes the defective region,
      wherein the extraction unit extracts the image of the characters according to a first predetermined rule when the defective region overlaps with the characters, and the extraction unit extracts the image of the characters according to a second predetermined rule different from the first predetermined rule when the defective region does not overlap with the characters; and
   an image display device that displays the image of the characters, extracted by the extraction unit and an image of the defective region such that both the images overlap with each other.

2. The image inspection system of claim 1, wherein when the defective region overlaps with the characters, the extraction unit extracts an image of one character which has the greatest overlap with the defective region among the characters.

3. The image inspection system of claim 1, wherein when the defective region does not overlap with the characters, the extraction unit extracts an image of at least two characters among the characters which are present adjacent to the defective region at upper, lower, left and right sides of the defective region.

4. The image inspection system of claim 3, wherein the extraction unit extracts an image of a character which is located within a distance of a predetermined value from the defective region on the recording medium.

5. The image inspection system of claim 3, wherein the extraction unit extracts the image of the characters at a cross-shaped region around the defective region.

6. An image inspection method, comprising:
   reading a formed image which is formed on a recording medium based on original image data to generate read image data;
   acquiring the original image data;
   comparing the generated read image data and the acquired original image data to determine whether or not the formed image includes a defective region; and extracting an image of characters which are present around the defective region from the read image data according to a predetermined rule when it is determined that the formed image includes the defective region, wherein the extracting the image of the characters occurs according to a first predetermined rule when the defective region overlaps with the characters, and occurs according to a second predetermined rule different from the first predetermined rule when the defective region does not overlap with the characters.

7. A non-transitory computer readable medium storing a program causing a computer to execute an image inspection process, the process comprising:

reading a formed image which is formed on a recording medium based on original image data to generate read image data;

acquiring the original image data;

comparing the generated read image data and the acquired original image data to determine whether or not the formed image includes a defective region; and extracting an image of characters which are present around the defective region from the read image data according to a predetermined rule when it is determined that the formed image includes the defective region, wherein the extracting the image of the characters occurs according to a first predetermined rule when the defective region overlaps with the characters, and occurs according to a second predetermined rule different from the first predetermined rule when the defective region does not overlap with the characters.

8. The image inspection system of claim 1, wherein the extraction unit extracts the image of the characters such that the image of the characters contains characters around the defective region from among all characters contained in the read image data.

* * * * *